United States Patent [19]
Braslow et al.

[11] Patent Number: 6,059,831
[45] Date of Patent: May 9, 2000

[54] METHOD OF IMPLANTING A UNI-CONDYLAR KNEE PROSTHESIS

[75] Inventors: Jonathon S. Braslow, Indian Wells, Calif.; Jeffrey King, Columbia City, Ind.

[73] Assignee: Biomet, Inc., Warsaw, Ind.

[21] Appl. No.: 09/281,867

[22] Filed: Mar. 31, 1999

[51] Int. Cl.$^7$ ............................. A61F 2/38; A61B 17/15
[52] U.S. Cl. ............................................. 623/20; 606/79
[58] Field of Search ............................. 606/79; 128/898; 623/18, 20

[56] References Cited

U.S. PATENT DOCUMENTS

| | | |
|---|---|---|
| D. 245,259 | 8/1977 | Shen . |
| 3,715,763 | 2/1973 | Link . |
| 3,774,244 | 11/1973 | Walker . |
| 3,852,830 | 12/1974 | Marmor . |
| 3,953,899 | 5/1976 | Charnley . |
| 3,958,278 | 5/1976 | Lee et al. . |
| 4,000,525 | 1/1977 | Klawitter et al. . |
| 4,034,418 | 7/1977 | Jackson et al. . |
| 4,055,862 | 11/1977 | Farling . |
| 4,085,466 | 4/1978 | Goodfellow et al. . |
| 4,178,641 | 12/1979 | Grundei et al. . |
| 4,309,778 | 1/1982 | Buechel et al. . |
| 4,355,429 | 10/1982 | Mittelmeier et al. . |
| 4,728,332 | 3/1988 | Albrektsson . |
| 4,743,261 | 5/1988 | Epinette . |
| 4,795,468 | 1/1989 | Hodorek et al. . |
| 4,838,891 | 6/1989 | Branemark et al. . |
| 5,019,103 | 5/1991 | Van Zile et al. . |
| 5,037,439 | 8/1991 | Albrektsson et al. . |
| 5,047,057 | 9/1991 | Lawes . |
| 5,047,058 | 9/1991 | Roberts et al. . |
| 5,092,895 | 3/1992 | Albrektsson et al. . |
| 5,122,144 | 6/1992 | Bert et al. . |
| 5,152,797 | 10/1992 | Luckman et al. . |
| 5,171,244 | 12/1992 | Caspari et al. . |
| 5,171,276 | 12/1992 | Caspari et al. . |
| 5,201,768 | 4/1993 | Caspari et al. . |
| 5,207,711 | 5/1993 | Caspari et al. . |
| 5,228,459 | 7/1993 | Caspari et al. . |
| 5,263,498 | 11/1993 | Caspari et al. ......................... 128/898 |
| 5,314,482 | 5/1994 | Goodfellow et al. ..................... 623/20 |
| 5,344,461 | 9/1994 | Phlipot . |
| 5,387,241 | 2/1995 | Hayes . |
| 5,458,637 | 10/1995 | Hayes . |
| 5,458,645 | 10/1995 | Bertin ....................................... 623/20 |
| 5,514,139 | 5/1996 | Goldstein et al. ........................ 606/79 |
| 5,514,143 | 5/1996 | Bonutti et al. ........................... 606/86 |
| 5,520,695 | 5/1996 | Luckman .................................. 606/88 |
| 5,531,793 | 7/1996 | Kelman et al. . |
| 5,549,688 | 8/1996 | Ries et al. . |
| 5,549,689 | 8/1996 | Epstein et al. . |
| 5,571,196 | 11/1996 | Stein ........................................ 623/20 |
| 5,578,039 | 11/1996 | Vendrely et al. ......................... 606/88 |
| 5,580,353 | 12/1996 | Mendes et al. . |
| 5,963,153 | 10/1990 | Noesberger et al. . |

OTHER PUBLICATIONS

"ACG Total Knee System, Unicondylar Surgical Overview" brochure, by Biomet, Inc.

*Primary Examiner*—Paul J. Hirsch
*Assistant Examiner*—Michael B. Priddy
*Attorney, Agent, or Firm*—Harness, Dickey & Pierce, P.L.C.

[57] ABSTRACT

The invention relates generally to a method for implanting a uni-condylar knee prosthesis. The method includes steps for preparing the bone surfaces of both the femoral and tibial effected compartments. The femoral compartment is prepared by making a distal cut, a posterior cuts and a posterior chamfer cut. Holes that correspond to posts on the femoral component are also prepared. The tibial compartment is prepared using a cutting guide and following the sclerotic bone formation on the proximal tibia. At least one hole is prepared in the sloped cut tibial surface to use for alignment when cementing the tibial component that has an alignment peg.

14 Claims, 8 Drawing Sheets

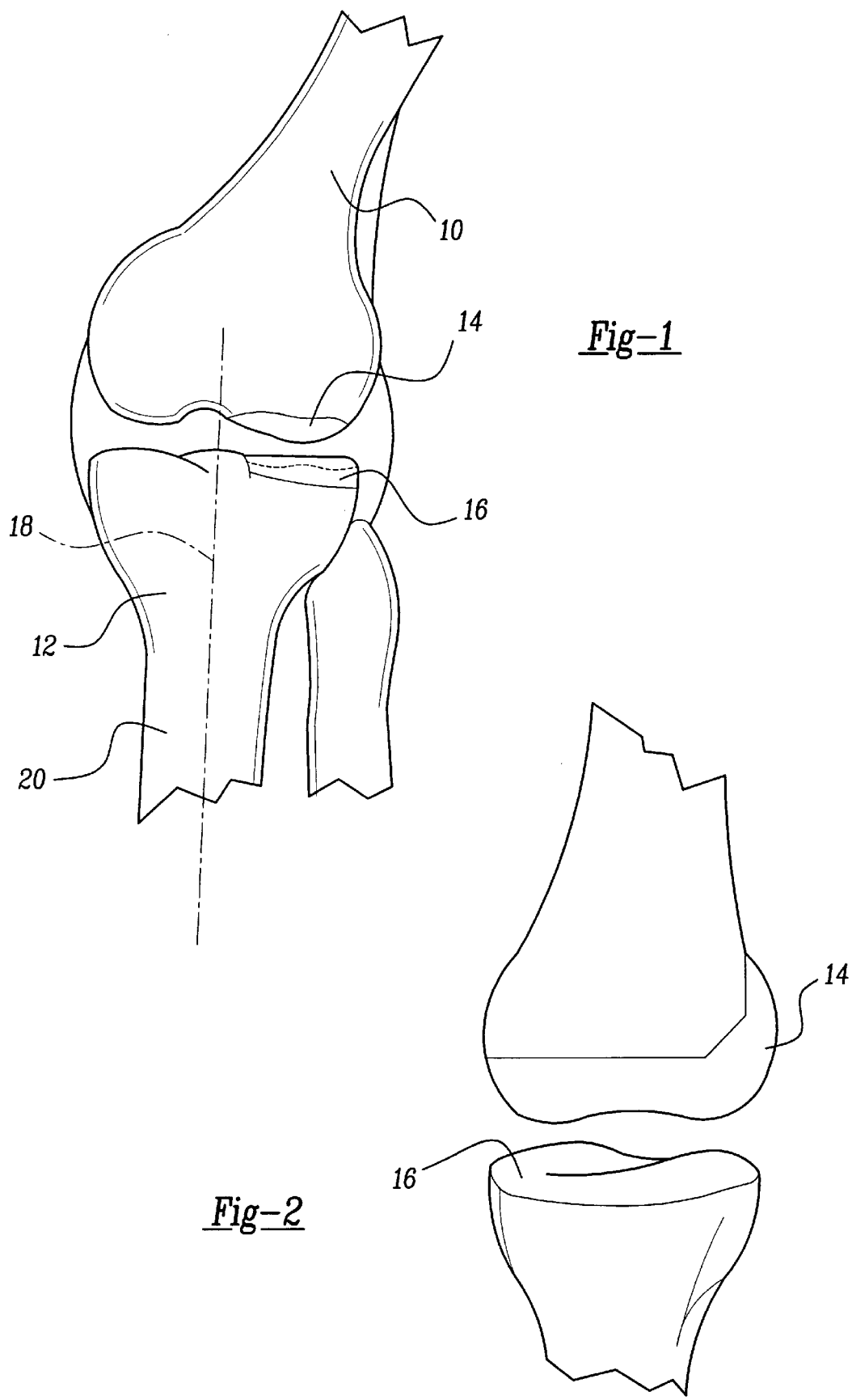

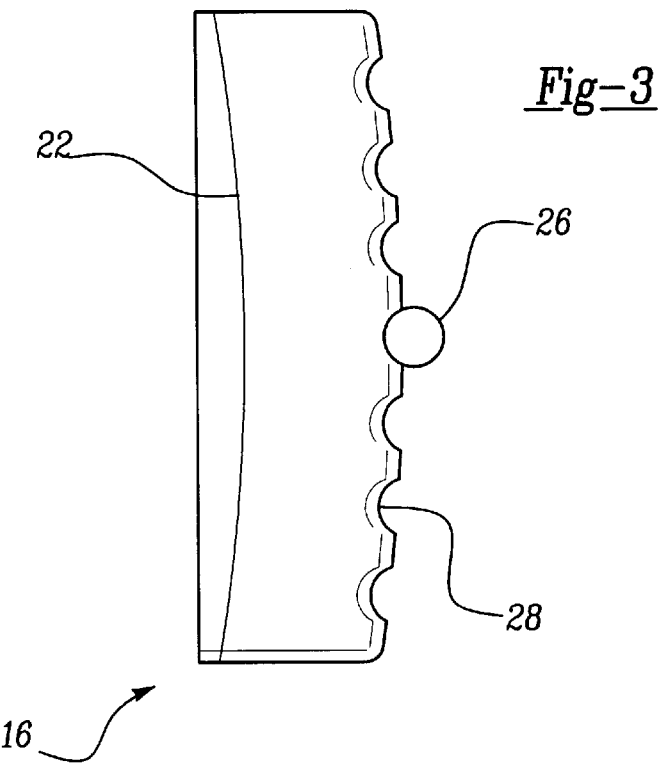
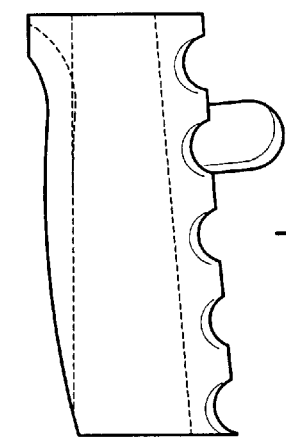
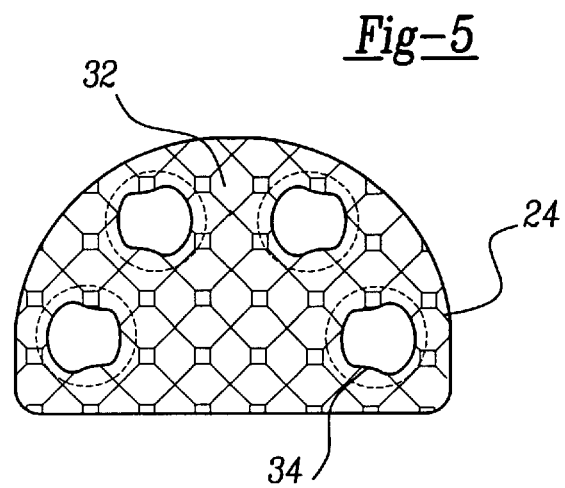

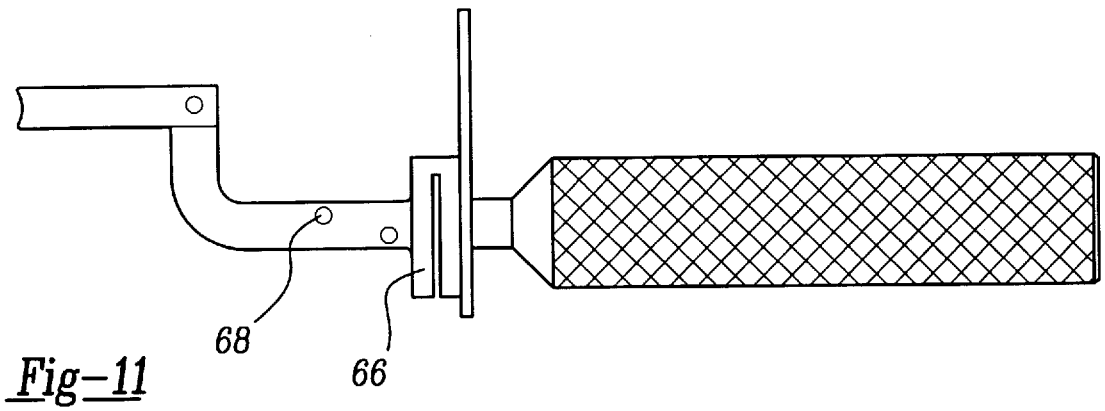
_Fig-11_
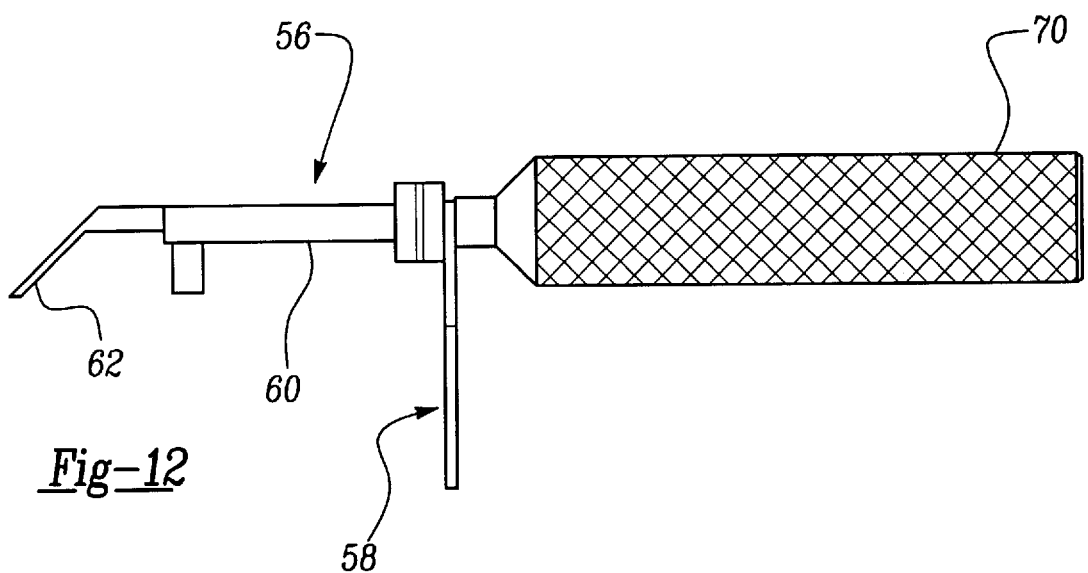
_Fig-12_
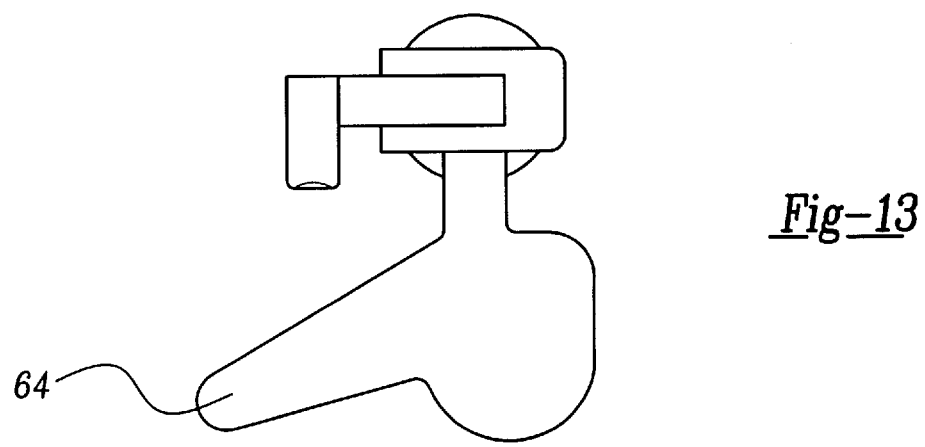
_Fig-13_

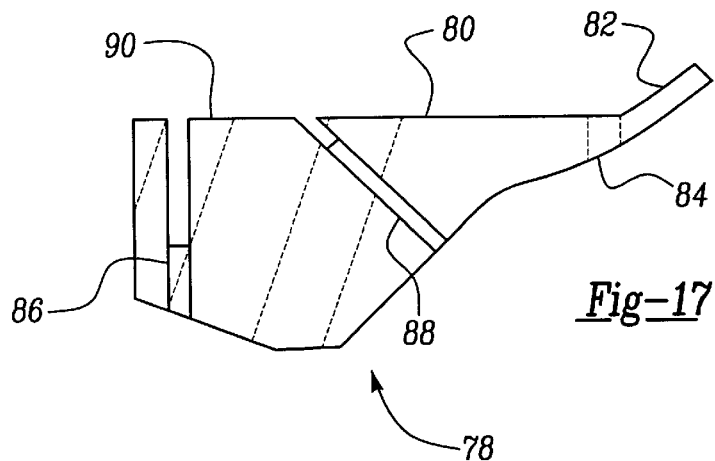
Fig-17
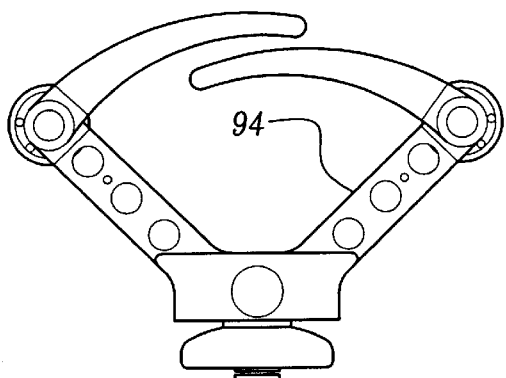
Fig-19
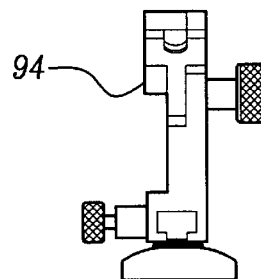
Fig-18
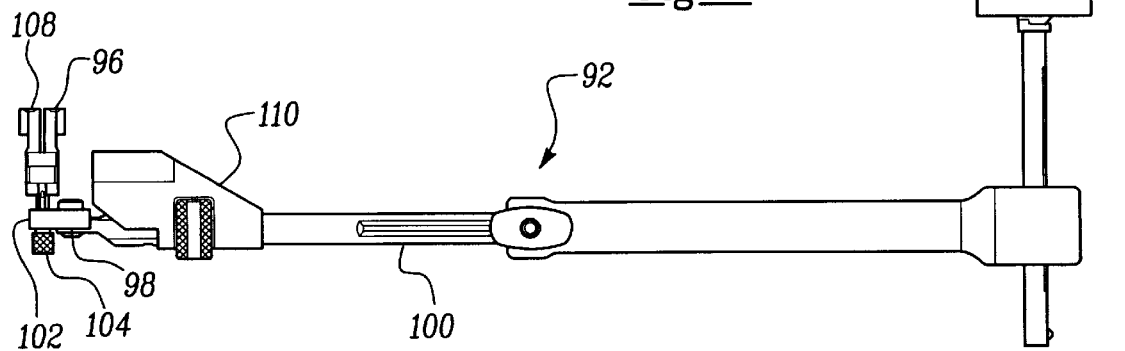

METHOD OF IMPLANTING A UNI-CONDYLAR KNEE PROSTHESIS

BACKGROUND OF THE INVENTION

1. Field of the Invention

The invention relates generally to a method for knee surgery, and more specifically, to a method for implanting a uni-condylar knee prosthesis.

2. Discussion of the Related Art

It is well known to perform surgery on a knee having arthritis or other bone degenerating diseases and to resurface the articulating junctions with a prosthetic device. One such method is to resurface only the portion of the knee joint that is effected using a uni-condylar knee prosthesis. One such device is shown in U.S. Pat. No. 3,852,830 to Marmor. Marmor teaches a uni-condylar femoral component and tibial component. The femoral component is thin and the bone is prepared using a bur. The tibial component has a generally flat distal surface and a horizontal cut on the tibia that is below the level of the defect. In fact, many other patents demonstrate a uni-condylar reconstruction surgery such as the patents shown in Table 1.

| Pat. No. | Inventor | Issue Date |
| --- | --- | --- |
| Des. 245,259 | Shen | Aug. 2, 1977 |
| 3,715,763 | Link | Feb. 13, 1973 |
| 3,774,244 | Walker | Nov. 27, 1973 |
| 3,953,899 | Charnley | May 4, 1976 |
| 3,958,278 | Lee | May 25, 1976 |
| 4,000,525 | Klawitter | Jan. 4, 1977 |
| 4,034,418 | Jackson | July 12, 1977 |
| 4,055,862 | Farling | Nov. 1, 1977 |
| 4,085,466 | Goodfellow | April 25, 1978 |
| 4,309,778 | Buechel | Jan. 12, 1982 |
| 4,355,429 | Mittelmeier | Oct. 26, 1982 |
| 4,728,332 | Albrektsson | Mar. 1, 1988 |
| 4,743,261 | Epinette | May 10, 1988 |
| 4,795,468 | Hodorek | Jan 3, 1989 |
| 4,838,891 | Branemark | June 3, 1989 |
| 4,963,153 | Noesberger | Oct. 16, 1990 |
| 5,037,439 | Albrektsson | Aug. 6, 1991 |
| 5,092,895 | Albrektsson | Mar. 3, 1992 |
| 5,122,144 | Bert | June 16, 1992 |
| 5,171,244 | Caspari | Dec. 5, 1992 |
| 5,171,276 | Caspari | Dec. 15, 1992 |
| 5,201,768 | Caspari | April 13, 1993 |
| 5,207,711 | Caspari | May 4, 1993 |
| 5,228,459 | Cas ari | July 20, 1993 |

The above patents all disclose a flat bone engaging surface and a cut on the tibia that is horizontal.

The patents disclose at least two ways that the tibia is prepared for the implant. The first is to make a horizontal cut starting just off of the midline in either the medial or lateral compartment of the knee, thereby preserving the anterior and posterior ligaments. The cuts vary in that one extends the remaining distance to the outermost portion of the tibia or stops short of cutting away the last portion of the cortical bone and uses the remaining bone to help secure the component from lateral movement. Some uni-condylar components have been reported to subside upon long-term use and subsequently must be revised. If the surgeon does not get the tibial component properly aligned and out to the hard cortical bone, the component may have a tendency to sink into the softer bone in the center region of the tibia plateau.

Other knee designs showing an angle or wedge concept exist such as those shown in the patents in Table 2.

| Pat. No. | Inventor | Issue Date |
| --- | --- | --- |
| 4,178,641 | Grundei | Dec. 18, 1979 |
| 5,019,103 | Van Zile | May 28, 1991 |
| 5,047,058 | Roberts | Sept. 10, 1991 |
| 5,152,797 | Luckman | Oct. 6, 1992 |
| 5,344,461 | Phlipot | Sept 6, 1994 |
| 5,387,241 | Hayes | Feb. 7, 1995 |
| 5,458,637 | Hayes | Oct. 7, 1995 |
| 5,531,793 | Kelman | July 2, 1996 |
| 5,549,688 | Ries | Aug. 27, 1996 |

The designs shown in the above-reference patents are designed to fill a gap created after making an initial horizontal or posterior sloped cut. The wedges are used to make up a gap that would otherwise have to be filled with bone cement or a lower horizontal cut would need to be made. The wedges are used mostly in revision surgery or in cases with severe bone degeneration that would require a large resection. There is no suggestion to use the wedge concept in a primary uni-condylar device. In fact, the wedge concept is used to make a thicker component.

Assignee of the present invention has previously commercialized a uni-condylar tibial component that uses a wedge shape that follows the slope of the sclerotic bone. The inventor of the present application recognized that an improvement could be made to make locating the tibial component on the tibial plateau easier when cementing on the device.

What is needed then is a method of implanting a uni-condylar knee prosthesis that follows the sclerotic bone that is present in a single compartment diseased knee and is easier to locate.

SUMMARY OF THE INVENTION

The present invention is a method of implanting a uni-condylar knee prosthesis in a patient having a femur and a tibia having a medial compartment and a lateral compartment. The tibia has a midline and an outer edge and a defect on one of the compartments that slopes down from the midline to the outer edge having sclerotic bone formation.

The steps of the method are to provide a femoral component having an articulating surface and a bone mating surface; providing a tibial component having a first surface operable to engage said femoral articulating surface, a bone mating surface opposite said first surface, a first edge and a second edge, said bone mating surface sloping from said first edge to said second edge and a post extending from the bone mating surface. Further steps include making at least one cut on the femur to accommodate the bone mating surface on the femoral component; making a cut on the tibia that slopes down along a line drawn from the midline to the outer edge of the tibia following the sclerotic bone formation. The method further includes the steps of forming at least one hole on the cut of the tibia that the post may extend into to align the tibial component on the tibia; and implanting the femoral and the tibial component onto the cut femur and the cut tibia. The method further comprises making a distal femoral cut on the femur. The method also comprises cementing the component.

BRIEF DESCRIPTION OF THE DRAWINGS

Still other advantages of the present invention will become apparent to those skilled in the art after reading the following specification and by reference to the drawings in which:

FIG. 1 is a front view of one embodiment of the invention implanted in a knee joint;

FIG. 2 is a side view of one embodiment of the invention implanted in a knee joint;

FIG. 3 is a side view of a tibial component of the invention;

FIG. 4 is an end view of a tibial component of the invention;

FIG. 5 is a bottom view of a tibial component of the invention;

FIG. 11 is a top view of a distal femoral cutting guide of the invention;

FIG. 12 is a front view of a distal femoral cutting guide of the invention;

FIG. 13 is an end view of a distal femoral cutting guide of the invention;

FIG. 17 is a side view of a chamfer guide of the invention;

FIG. 18 is a side view of a tibial-cutting guide of the invention;

FIG. 19 is a top view of a tibial-cutting guide of the invention;

DETAILED DESCRIPTION OF THE PREFERRED EMBODIMENT

Figure 6:
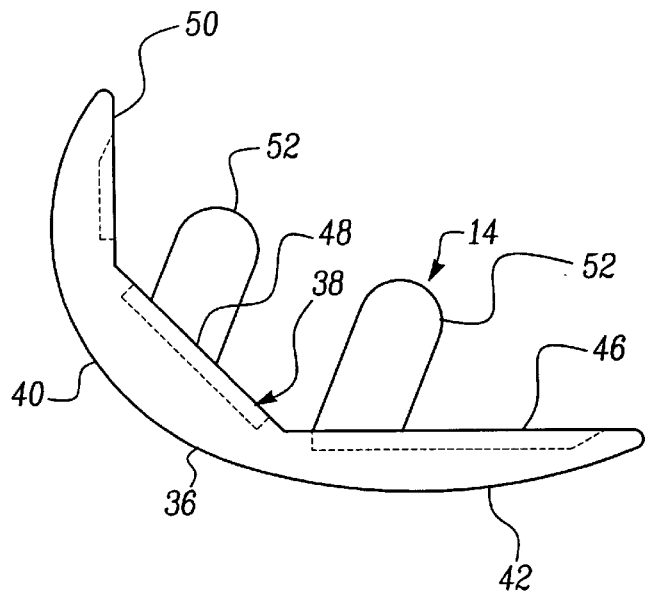
FIG. 6 is a side view of a femoral component of the invention.

The preferred embodiment herein described is not intended to be exhaustive or to limit the invention to the precise form disclosed. This description is limited to the preferred embodiment only and is intended to describe the invention to enable one of ordinary skill in the art to practice the invention.

Referring now to FIGS. 1 and 2, a uni-condylar knee prosthesis implanted using the method of the invention is shown. The femur 10 is shown in combination with a tibia 12. The femur 10 has a femoral component 14 implanted therein. The tibia has a tibial component 16 implanted therein. While a left lateral surgery is shown, it is known that the method will apply to both medial and lateral components, as well as left and right knees. A midline 18 is shown on the tibia 12 that extends along the shaft 20 of the tibia 12.

Referring now to FIG. 3, the tibial component 16 is shown in detail. The tibial component 16 has an upper articulating surface 22 that engages femoral component 14. The top view shows the perimeter 24 is a D-shaped design. A peg 26 extends from a bone mating surface 28 that is opposite articulating surface 22. Bone mating surface 28 is angled relative to the articulating surface 22 and more specifically when implanted the surface is angled relative to the tibial plateau. The preferred embodiments have an angle 30 of about 5 degrees (5°) to 10 degrees (10°), although it is recognized that other angles could be used. The bone mating surface 28 has a waffle pattern 32 or roughened surface that helps with bone cement interdigitation. The articulating surface 22 is intended to mate with an articulating surface of femoral component 14 and thus should be relatively horizontal. If the articulating surface of the femoral component and tibial component were spherical, it would be unnecessary to provide a slope on the bone mating surface 28. Since alignment of the spherical surfaces is difficult in the knee, it is desirable to flatten at least one of the articulating surfaces leading to the need for angle 30 to allow the bone mating surface 28 to follow the sclerotic bone formation on the tibial plateau. A set of holes 34 are present on the bone mating surface 28 that allow for further bone cement interdigitation.

Figure 7:
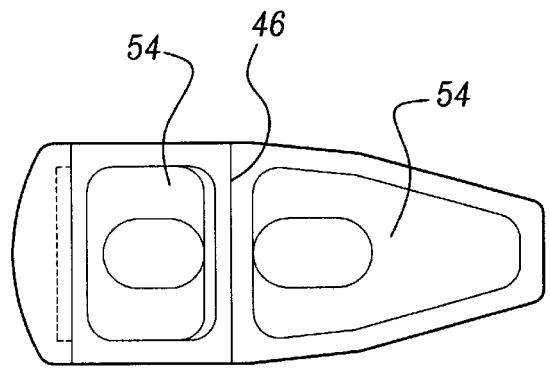
FIG. 7 is top view of a femoral component of the invention.
Figure 8:
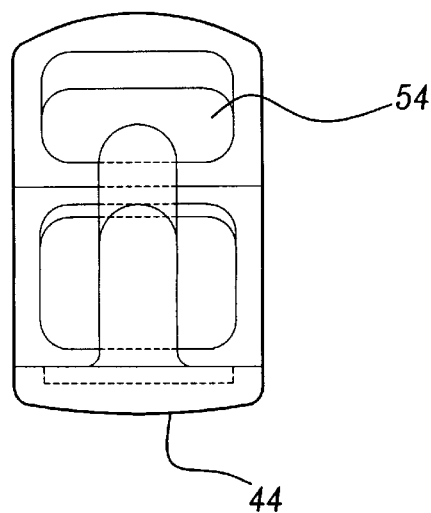
FIG. 8 is an end view of a femoral component of the invention.
Figure 9:
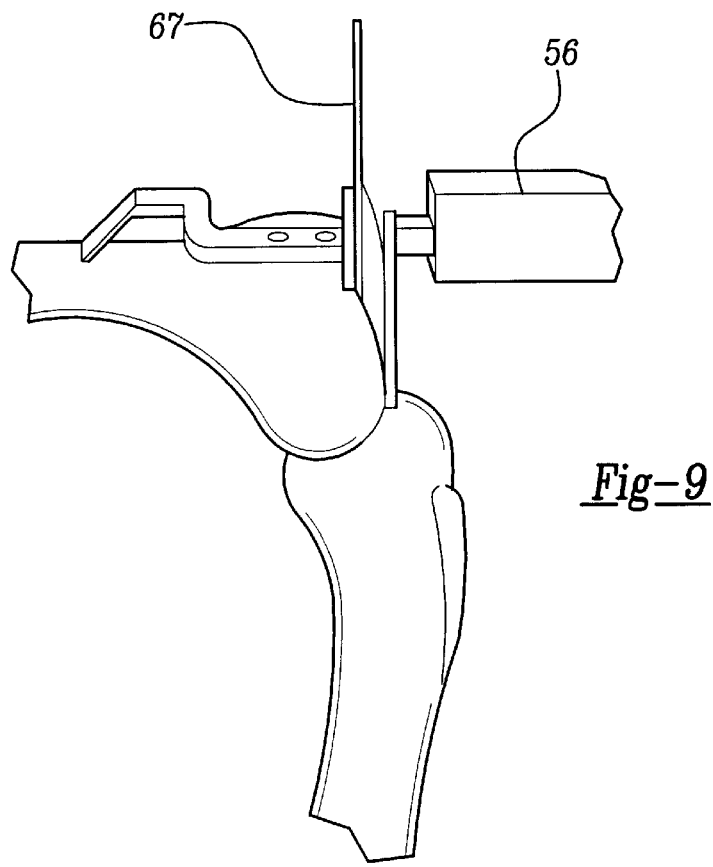
FIG. 9 is a side view of a distal femoral cutting guide of the invention mounted on a femur.
Figure 10:
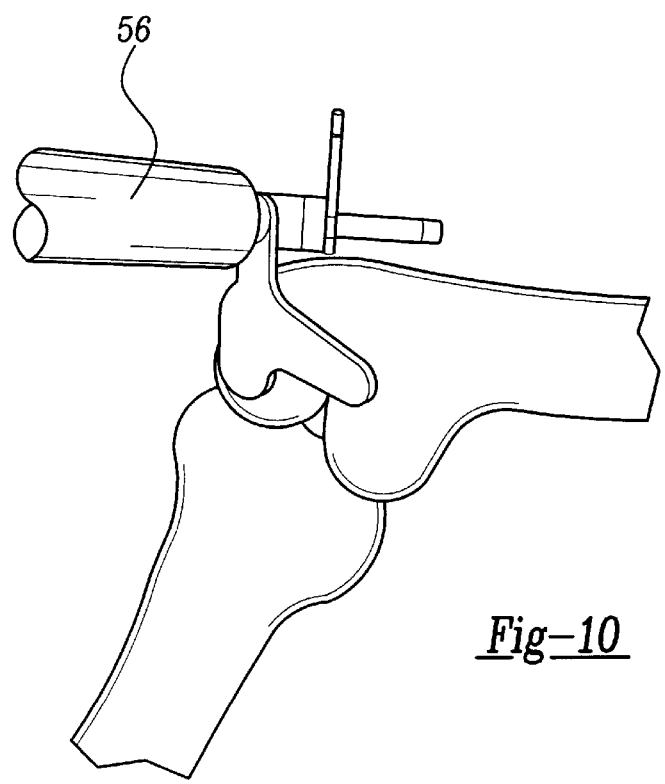
FIG. 10 is a perspective view of a distal femoral cutting guide of the invention mounted on a femur.

Referring now to FIGS. 6–8, the femoral component 14 is shown. The femoral component 14 is designed to resurface the distal and posterior portion of one of the femoral condyles of femur 10. The femoral component 14 has an articulating surface 36 and a bone mating surface 38. The articulating surface 36 in the preferred embodiment has a pair of radial surfaces 40 and 42 that are tangent forming a smooth flowing surface when viewed from the lateral direction. In the other plane, the distal portion of the femoral component 14 has a radius 44 that is larger than and blends with radius 46 that is present on the posterior portion. This allows for more movement between the femur 10 and tibia 12 when in flexion than in extension similar to the natural knee. The bone mating surface 38 is comprised of a distal surface 46, a posterior surface 48, and a posterior chamfer surface 50. Extending from the bone mating surface 38 is a pair of pegs 52. The pegs 52 aid in alignment and in stability. Relieved sections 54 are present on the bone mating surface 38 to allow for a build up of bone cement.

The method of implantation for the uni-condylar knee prosthesis will now be described including a description of the instruments used for the method. Referring now to FIGS. 9–13, a midline incision or a medial parapatellar incision is made to open the knee as is known by those skilled in the art. After exposure of the joint, a distal femoral resection guide 56 is placed over the anterior distal femur 10. The resection guide 56 has a distal referencing surface 58 and an anterior referencing surface 60. The anterior referencing surface 60 has an extension 62 that is passed proximal on the femur 10 and rests against the anterior portion of the shaft. Distal referencing surface 58 has a flat stop guide 64 that extends to the later condyle. While maintaining the referencing surfaces in contact with the bone, a saw guide surface 66 is positioned over the effected distal condyle and a saw blade 67 is passed through the guide surface 66. The distal resection guide 56 is designed to remove about 5 mm of distal femur. Pin holes 68 on the anterior referencing surface 60 are used to stabilize the resection guide 56 while passing the saw 67 through the saw guide surface 66. A handle 70 extends from one end of the resection guide 56 to manipulate the device.

Figure 14:
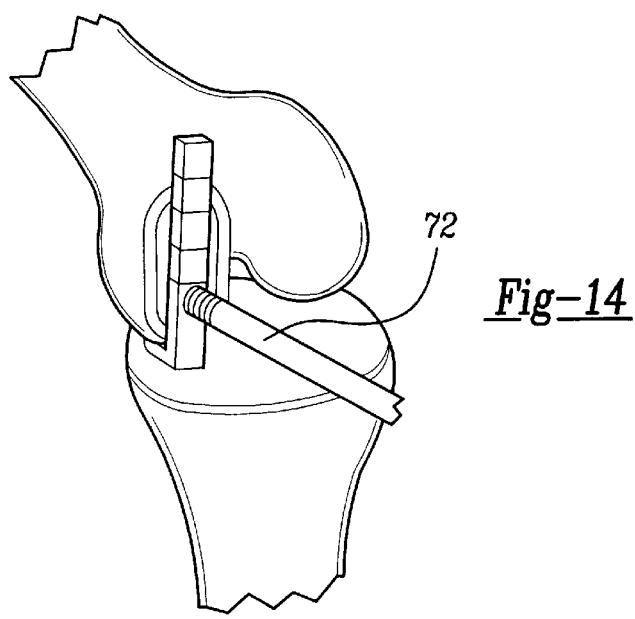
FIG. 14 is a perspective view of a distal femoral sizing guide of the invention placed on a femur.
Figure 15:
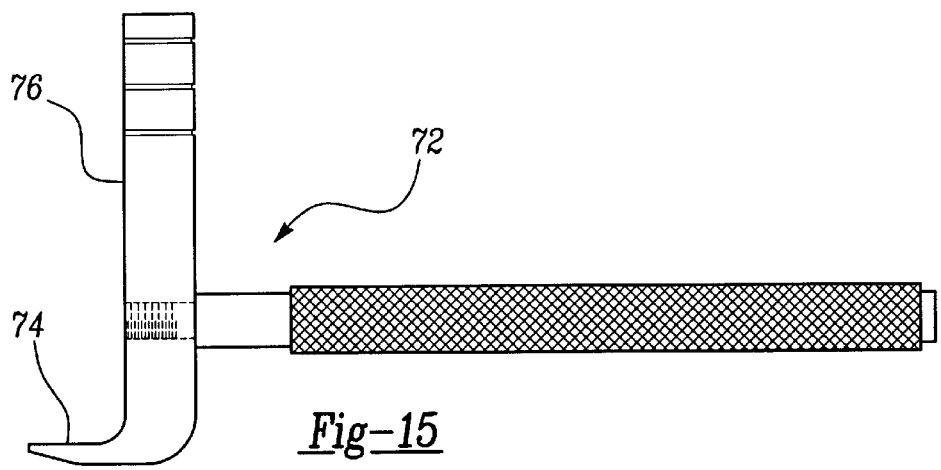
FIG. 15 is a side view of a distal femoral sizing guide of the invention.

After completing the distal femoral cut, the size of the femoral condyle is measured using a sizing guide 72. Referring to FIGS. 14 and 15, the sizing guide 72 has a posterior condyle referencing surface 74 and a distal referencing surface 76. The size is read where the anterior portion of the distal cut meets the sizing guide 72. In the preferred embodiment, the femoral component 14 is available in three sizes. After sizing the femur 10, the center of the compartment of the tibia 12 to be resurfaced is marked. A mark is placed on the posterior femoral compartment directly above the mark on the tibia, while the knee is in 90 degrees of flexion. The knee is then extended and the center of the condyle is marked where the distal cut runs out on the anterior region.

Figure 16:
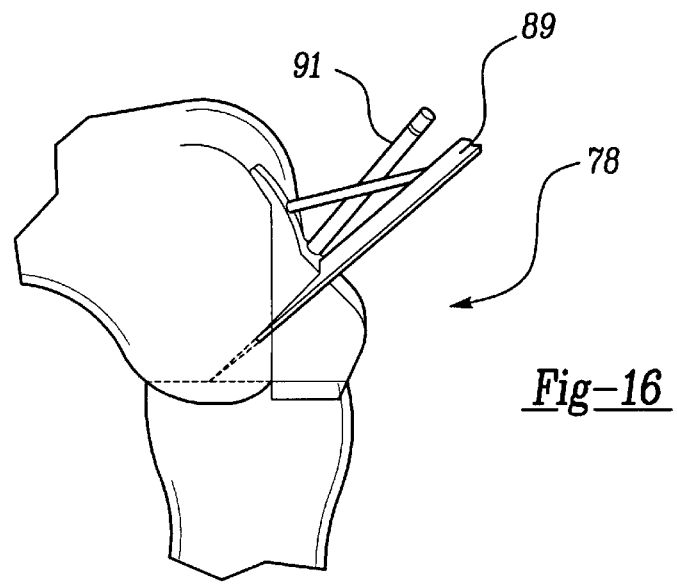
FIG. 16 is a side view of a chamfer guide of the invention mounted on a femur.

A chamfer guide 78, shown in FIGS. 16 and 17, is used to complete the femoral cuts. The guide 78 has a distal femoral contacting surface 80 and an anterior condyle referencing surface 82. The guide 78 is placed against the distal femur with the previously referenced surfaces 80 and 82 contacting the femur 10, as shown in FIG. 16. Pin holes 84 are used to place pins into the bone to secure the guide 78 in place while making the saw cuts. The guide 78 has a pair of saw guide slots 86 and 88 that are used to guide the saw blade 89 when making the posterior cut and the posterior chamfer cut. The cuts are designed to correspond to the bone mating surfaces 50 and 48. The chamfer guide 78 also has two larger holes 90 that are used to guide a drill 91 for forming holes in the femur that the pegs 52 on the femoral component 14 engage.

Figure 20:
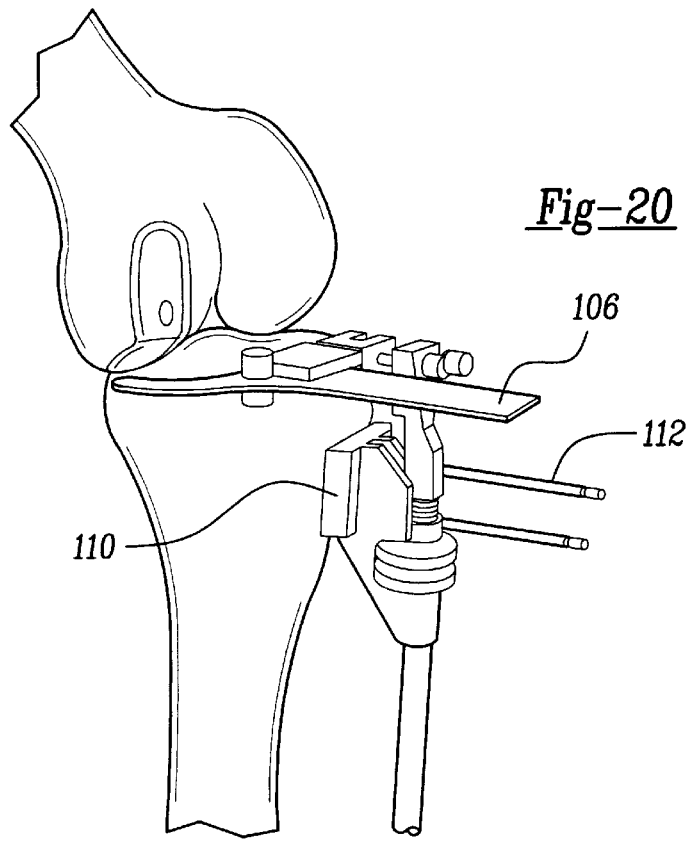
FIG. 20 is a perspective view of a tibial-cutting guide of the invention mounted on a tibia.

The effected tibial compartment is now addressed although it will be appreciated that the preparation may be completed in opposite order. The tibia 12 is resected using a tibial-cutting guide 92, shown in FIGS. 18–20, having an ankle clamp 94 and a cutting head 96. The cutting head 96 is mounted on a pivot 98 that allows the cutting head 96 to pivot for use as a lateral or medial cuffing jig. A block 102 extends from a telescoping shaft 100 that the pivot 98 is mounted to. The block 102 has a pair of pins 104 extending therefrom. The pins 104 function to allow the cutting head 96 to pivot and be locked into place by engaging one of a set of holes on the cutting head. The preferred embodiment allows the cutting head 96 to be locked into a horizontal position, having about 5 degrees of tilt, or 10 degrees of tilt. The positions are mirrored when using the opposite side. A sight guide 106 is used to eye the cutting depth of the tibial-cutting guide 92. The sight guide 106 is curved and fits through saw guide slot 108. The tibial-cutting guide 92 is used to cut the proximal tibia along the sclerotic bone that has formed on the tibia 12. The sclerotic bone formation is not removed and is used to support the tibial component 16. The tibial-cutting guide 92 can also be used to put a posterior slope on the tibial plateau. The posterior slope is adjusted by raising or lowering the height of the ankle clamp 94 relative to the cutting head 96. The telescoping shaft 100 has a body 110 on the proximal end. The body has holes for engagement of pins 112 to stabilize the cutting guide 92 when passing the saw blade through the saw guide slot 108. The cut is completed after the cutting guide 92 is removed. The saw blade is passed along the tibial eminence preserving the posterior and anterior cruciate ligaments and the portion of bone is removed.

Figure 21:
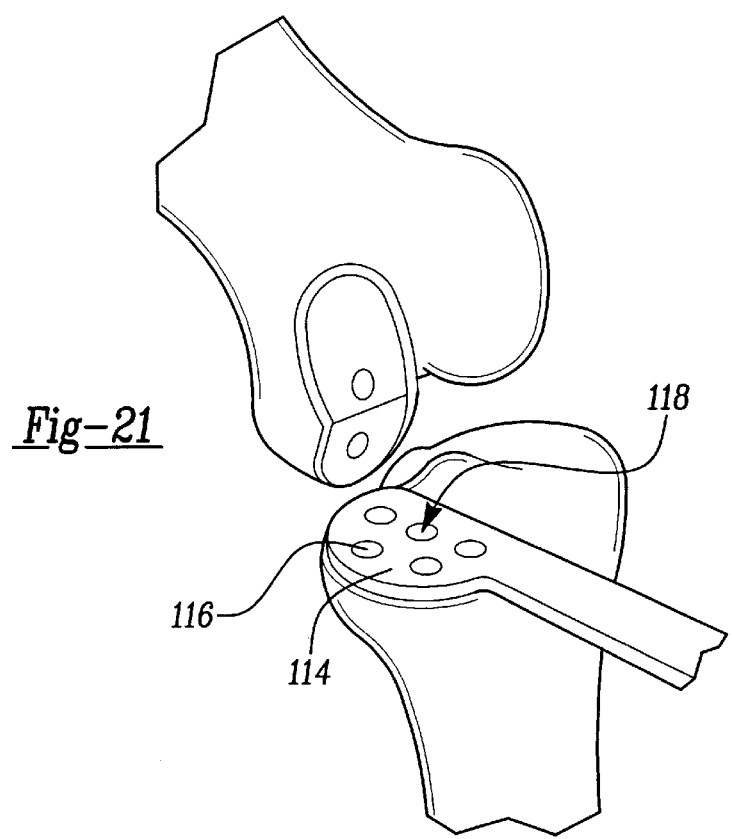
FIG. 21 is a perspective view of a tibial template/drill guide of the invention mounted on a tibia.

The resectioned tibia is then sized using a template 114, shown in FIG. 21. The templates 114 are available in sizes corresponding to the tibial components 16. The template 114 also has holes 116 that a drill passes through to create cement holes for increased interdigitation. A different hole 118 that corresponds to the post 26 is operable to guide a drill bit to prepare a hole to receive the post 26. The hole and post 26 combine to align the tibial component 16 on the tibial plateau when cementing the component in place.

Both components are cemented in using conventional cementing techniques that are well known to those skilled in the art. The wound is then closed and post-operative care is given.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

What is claimed is:

1. A method of implanting a uni-condylar knee prosthesis in a patient having a femur and a tibia with a medial compartment and a lateral compartment, the tibia having a midline and an outer edge with a defect on the tibia that results in a sclerotic bone formation that slopes down from the midline to the outer edge of the tibia, said method comprising:

providing a femoral component and a tibial component, said tibial component having a proximal surface operable to engage said femoral component and a distal surface operable to engage the tibia, said distal surface declining from the midline to the outer edge, wherein said tibial component is thinner at the midline than at the outer edge and includes at least one peg extending from said distal surface;

making a set of bone cuts on the femur that correspond to said femoral component;

making a minimal cut on the tibia that slopes from the midline down toward the outer edge following the defect on the tibia to preserve the sclerotic bone formation;

forming at least one hole in the tibia that corresponds to said peg on said tibial component to allow for alignment;

implanting said femoral component; and aligning and implanting said tibial component on top of the remaining sclerotic bone formation to avoid migration of said tibial component.

2. The method of implanting a uni-condylar knee prosthesis of claim 1, further comprising the step of cementing said femoral and tibial components to the bone.

3. The method of implanting a uni-condylar knee prosthesis of claim 1, wherein said step of making a set of bone cuts on the femur includes the step of making a distal femoral cut.

4. The method of implanting a uni-condylar knee prosthesis of claim 3, wherein said step of making a set of bone cuts on the femur further includes the step of making a posterior cut and a posterior chamfer cut that intersects said posterior cut and said distal femoral cut.

5. The method of implanting a uni-condylar knee prosthesis of claim 3, wherein the femur is measured for size after making said distal cut.

6. The method of implanting a uni-condylar knee prosthesis of claim 1, wherein said step of providing a femoral component and a tibial component includes the step of providing components of different sizes to better fit the femur and tibia.

7. A method of implanting a uni-condylar knee prosthesis in a patient having a femur and a tibia with a medial compartment and a lateral compartment, the tibia having a midline and an outer edge and a defect on the tibia that slopes down from the midline to the outer edge having sclerotic bone formation, said method comprising:

providing a femoral component having a first articulating surface and a first bone mating surface;

providing a tibial component having a second articulating surface operable to engage said first articulating surface and a second bone mating surface opposite said second articulating surface, a first edge and a second edge, said second bone mating surface sloping from said first edge to said second edge and having a post extending from said second bone mating surface;

making at least one cut on the femur to accommodate said first bone mating surface on said femoral component;

making a cut on the tibia that slopes down along a line drawn from the midline to the outer edge of the tibia following the sclerotic bone formation;

forming at least one hole on said cut of the tibia that said post may extend into to align said tibial component on the tibia; and implanting said femoral component and said tibial component onto the cut femur and the cut tibia.

8. The method of implanting a uni-condylar knee prosthesis of claim 7, wherein said step of making at least one cut on the femur is a distal femoral cut.

9. The method of implanting a uni-condylar knee prosthesis of claim 8, further comprising a step of measuring the femur to determine the size of the femur.

10. The method of implanting a uni-condylar knee prosthesis of claim 7, wherein said step of providing a femoral component further comprises providing multiple sizes to accommodate different sized femurs.

11. The method of implanting a uni-condylar knee prosthesis of claim 7, wherein said step of providing a tibial component further comprises providing multiple sizes to accommodate different sized tibias.

12. The method of implanting a uni-condylar knee prosthesis of claim 7, wherein said step of providing a tibial component further comprises providing different slopes on said second bone mating surface of said tibial component to allow for substantially following an existing slope of the tibia.

13. The method of implanting a uni-condylar knee prosthesis of claim 7, further comprising a step of cementing said femoral component and said tibial component to the femur and tibia.

14. The method of implanting a uni-condylar knee prosthesis of claim 13, further comprising providing a roughened bone engaging surface to allow cement interdigitation.

* * * * *

UNITED STATES PATENT AND TRADEMARK OFFICE
CERTIFICATE OF CORRECTION

PATENT NO.   : 6,059,831
DATED        : May 9, 2000
INVENTOR(S)  : Jonathon S. Braslow It is certified that error appears in the above-identified patent and that said Letters Patent is hereby corrected as shown below:

Title page,
Item [56], Reference Cited, "5963153" should be -- 4963153 --

Item [57], ABSTRACT, line 6, "cuts" should be -- cut --.

Column 1,
Line 16, "effected" should be -- affected --
Line 48, "Cas ari" should be -- Caspari --.

Column 3,
Line 14, after "is" insert -- a --.

Column 6,
Line 61, after "that" insert -- results in sclerotic bone formation that --.
Lines 62-63, delete "having sclerotic bone formations" and insert -- of the tibia --.

Signed and Sealed this

Thirtieth Day of April, 2002

*Attest:*

*Attesting Officer*

JAMES E. ROGAN
*Director of the United States Patent and Trademark Office*